(12) United States Patent
Plewa et al.

(10) Patent No.: US 7,875,845 B2
(45) Date of Patent: Jan. 25, 2011

(54) AUTOMATED EXTRACTION AND PURIFICATION OF SAMPLES USING OPTICAL TWEEZERS

(75) Inventors: Joseph S. Plewa, Park Ridge, IL (US);
Evan B. Tanner, Chicago, IL (US);
Daniel M. Mueth, Chicago, IL (US);
Crystal J. Duke, Chicago, IL (US);
Kevin J. Ehrenreich, San Francisco, CA (US)

(73) Assignee: Arryx, Inc., Chicago, IL (US)

( * ) Notice: Subject to any disclaimer, the term of this patent is extended or adjusted under 35 U.S.C. 154(b) by 1214 days.

(21) Appl. No.: 11/298,565

(22) Filed: Dec. 12, 2005

(65) Prior Publication Data
US 2006/0134603 A1    Jun. 22, 2006

Related U.S. Application Data

(60) Provisional application No. 60/634,980, filed on Dec. 13, 2004, provisional application No. 60/635,164, filed on Dec. 10, 2004.

(51) Int. Cl.
*H01S 1/00* (2006.01)
*C12Q 1/00* (2006.01)
*G01N 1/18* (2006.01)
*G01N 21/00* (2006.01)

(52) U.S. Cl. ............... 250/251; 210/732; 210/800; 210/802; 422/82.05; 435/4; 435/173.1; 436/177; 703/11

(58) Field of Classification Search .............. None
See application file for complete search history.

(56) References Cited

U.S. PATENT DOCUMENTS 5,392,155 A    2/1995    Tamari (Continued)

FOREIGN PATENT DOCUMENTS

DE    19952322    5/2001

(Continued)

OTHER PUBLICATIONS

Isadora B. Stehlin. "FDA's Forensic Center: Speedy, Sophisticated Sluething" 1995, FDA website: http://www.fda.gov/fdac/features/695_forensic.html.

(Continued)

*Primary Examiner*—Krishnan S Menon
*Assistant Examiner*—Dirk Bass
(74) *Attorney, Agent, or Firm*—Jean C. Edwards, Esq.; Akerman Senterfitt (57) ABSTRACT

An apparatus and method for purifying a forensic sample using an automated extraction and purification system includes optical tweezers; an input channel through which the sample is introduced; a chamber which receives the sample from the input channel; a collection channel through which selected particles of the sample are removed; and an output through which unselected particles of the sample are removed. At least one buffer input channel is provided. The input channel may allow sedimentation of the sample into the chamber by gravity. In another arrangement, the system includes an optical trapping system; a first channel through which the sample is introduced; a second channel through which buffer is introduced; wherein the optical tweezers are used to move selected particles of the sample from the first channel to the second channel. The selected particles may be sperm. The optical tweezers preferably utilize holographic optical trapping.

19 Claims, 4 Drawing Sheets

U.S. PATENT DOCUMENTS

| | | |
|---|---|---|
| 6,005,964 A | 12/1999 | Reid et al. |
| 6,055,106 A | 4/2000 | Grier et al. |
| 6,624,940 B1 | 9/2003 | Grier et al. |
| 2002/0121443 A1* | 9/2002 | O'Connell ............... 204/547 |
| 2003/0032204 A1* | 2/2003 | Walt et al. ............... 436/518 |
| 2004/0089798 A1 | 5/2004 | Gruber et al. |
| 2005/0061962 A1* | 3/2005 | Mueth et al. ............ 250/251 |

FOREIGN PATENT DOCUMENTS

| | | |
|---|---|---|
| DE | 10313760 | 6/2004 |
| GB | 2371858 | 8/2002 |
| WO | WO 88/07199 | 9/1988 |
| WO | WO 01/31315 A1 | 5/2001 |

OTHER PUBLICATIONS

Hirokazu Kusakabe et al., "Maintenance of Genetic Integrity in Frozen and Freeze-Dried Mouse Spermatoza" Proceedings of the National Academy of Sciences, vol. 98, No. 24. p. 13501-13506, Nov. 20, 2001.

Mattias Goksor et al.; Optical Manipulation in Combination with Multiphoton Microscopy for Single-Cell Studies; Applied Optics; Sep. 2004; pp. 4831-4837 vol. 43, No. 25; US.

* cited by examiner

AUTOMATED EXTRACTION AND PURIFICATION OF SAMPLES USING OPTICAL TWEEZERS

CROSS-REFERENCE TO RELATED APPLICATIONS

The present invention claims priority from U.S. Provisional Patent Application No. 60/635,164 filed Dec. 10, 2004, and 60/634,980 filed Dec. 13, 2004, the entire contents of which are herein incorporated by reference.

BACKGROUND OF THE INVENTION

1. Field of the Invention

The present invention relates to the automated extraction and purification of a sample using optical tweezers. In particular, the present invention relates to the automated extraction and purification of sperm from samples—particularly sexual assault forensic samples (i.e., swabs, fabric, etc.) using holographic optical trapping.

2. Description of the Related Art

Forensic testing requires critical care for maintaining the chain of custody. Moreover, in areas such as forensic DNA testing, proper handling of the evidence can prevent contamination of the DNA sample, allowing effective PCR (polymerase chain reaction) amplification of DNA from isolated cells and STR (short tandem repeats) analysis.

Because of the nature of the sample collection in cases of rape, for example, separation of the victim's DNA from the perpetrator's DNA is essential for performing a test. Epithelial cells from the victim contain DNA that frequently mix with the DNA inside the sperm of the perpetrator upon testing, confusing the results. Currently, the present technique for separating sperm from epithelial cells, which is widely used, is a sequence of washing steps designed to selectively break open the membranes of one or the other cell type, then washing out of the DNA from that cell type, and then lysing of the second cell type and collection of the second DNA sample. Due to the imprecision of this technique and the variability in the cells and the cell/sample histories, this lysing/washing technique frequently gives STR results with signatures of both the victim and assailant mixed. If the assailant is unknown, a DNA/STR database is used to locate/identify the assailant. For these cases, the mixed STR signatures prevent the use of the database and linking of the forensic data to (a) other crimes, and (b) a possible assailant.

Accordingly, a method and apparatus which would enable three-dimensional manipulation of large numbers of objects with great precision, which could move the objects, such as cells, over large distances, or rotate the objects for analysis from multiple angles, is desired. It would also be desirable to keep a visual record of the processing of the sample, such as by taking images and/or video. It would also be advantageous to have a method and apparatus which could perform this manipulation in sealed chambers, for example, providing no possibility for cross-contamination, and without causing damage to the objects. Further, it would be of benefit to preserve all the materials collected, for storage and potentially further analysis at a later time.

SUMMARY OF THE INVENTION

The present invention establishes the use of optical tweezers as the core of an automated isolation process which may be practically deployed for forensic work in isolating sperm from samples, for genetic analysis or for other forensic applications. In particular, the present invention relates to an automated machine for isolating a purified sample of sperm from a complex sample containing sperm, epithelial cells, and other materials, for determination of genetic make-up of the sperm DNA, using optical trapping or holographic optical trapping (HOT).

In particular, Holographic Optical Trapping (HOT) technology can revolutionize the handling of forensic samples, by performing high-speed, massively parallel sorting, to automatically separate sperm and epithelial cells.

Specifically, HOT splits up a single laser beam holographically into multiple optical traps, each computer-controlled (and therefore, positionable and movable) in three dimensions. A HOT system does this by employing a spatial light modulator (often a liquid crystal device), to encode a hologram. A computer interface writes the desired holographic pattern to the spatial light modulator. The laser beam then bounces off the spatial light modulator, and upon entering a microscope objective lens, splits into the desired pattern of traps. The computer-generated pattern can be quickly updated to play an animated sequence of laser-traps, pulling particles along user-defined paths. The holographic control even allows trap type and properties to be adjusted to allow manipulation of particles like metals or absorbing particles. The net result is a complete micro- or nano-manipulation system, providing the user with the ability to move large numbers of cells or other particles, simultaneously, along arbitrary paths in three dimensions. The addition of a CCD camera and image processing provides a machine-vision guided system that can automatically execute sophisticated manipulation.

Since large arrays of optical traps can be created, HOT can be used to create light filters with advantages far beyond standard material-based filters. These light filters can sweep away unwanted materials, purifying or sorting samples to provide desired components. HOT filters never clog, provide no back-pressure, and can be tuned to not harm materials, like cells. Furthermore, the versatility of the computer-controlled filter means that a wide variety of materials may be sorted.

Thus, a HOT system combines two powerful technologies—lasers and holography—to enable three-dimensional manipulation of large numbers of objects with great precision. Samples like cells can be moved over large distances, or rotated for analysis from multiple angles. Because laser beams are employed to effectively levitate the objects, manipulation can occur in sealed chambers, minimizing or eliminating cross-contamination. Furthermore, manipulation of living or inanimate matter with light is extremely gentle, minimizing concerns about damage to particles. Also, a holographic laser manipulation system can be used in either a user-interactive mode or can be programmed for a virtually unlimited set of manipulation tasks.

The invention described herein is an apparatus and method that allows uncontaminated introduction of a forensic sample, introduces the sample into a container for extraction using optical trapping or holographic optical trapping, and closes off that container in order to limit contamination.

In addition, the present invention allows for a visual record of the processing of a sample. Still further, the present invention allows for the production of a statistical record representing the contents of the sample.

Thus, this apparatus will generally find wide applicability in handling of forensic evidence of a variety of types beyond sperm using optical trapping and holographic optical trapping.

In one embodiment consistent with the present invention, a method and apparatus of purifying a forensic sample in an automated extraction and purification system which uses optical tweezers, includes an optical trapping system; an input channel through which the sample is introduced; a chamber which receives the sample from the input channel; a collection channel through which selected particles of the sample are removed; and an output through which unselected particles of the sample are removed.

In one embodiment, at least one buffer input channel is provided, through which buffer is introduced into the system.

In yet another embodiment, a barrier is provided over which the selected particles are moved into the output.

In yet another embodiment, the output is at least one output channel.

In yet another embodiment, the input channel allows sedimentation of the sample into the chamber by gravity.

In yet another embodiment, a flow of buffer into the chamber from the buffer input channel, and a flow of the sample into the chamber from the input channel, can be continuous or intermittent.

In yet another embodiment, a lower surface of the chamber is treated with an anti-stick coating to prevent sticking of the sample to the surface.

In yet another embodiment, a purging flow is provided to remove the unselected particles through the output, and the chamber is cleaned using a purging flow.

In yet another embodiment consistent with the present invention, an automated extraction and purification apparatus for purifying a forensic sample using optical tweezers, includes an optical trapping system; a first channel through which the sample is introduced; a second channel through which buffer is introduced; wherein the optical tweezers is used to move selected particles of the sample from the first channel to the second channel. In one embodiment, a barrier which separates the first channel from the second channel. An anti-stick coating is applied to walls of the first channel and the second channel.

In all embodiments, a window is provided through which imaging and optical tweezing is performed. An imaging camera images the sample, and is controlled by a computer.

In yet another embodiment, the selected particles are sperm, and they are collected in a separate and sealed container, such as a removable vial.

In yet another embodiment, at least the channels are disposed on a movable stage.

In yet another embodiment, imaging of the particles using the imaging camera, is automated.

In yet another embodiment, the optical tweezers utilize holographic optical trapping, but may also utilize non-holographic optical trapping.

In yet another embodiment, a report is automatically generated to provide information on the selected particles.

In yet another embodiment, a visual record of the processing of the sample can be maintained by the computer.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

The present invention relates to an automatic extraction and purification System using optical trapping or holographic optical trapping, which is used to handle forensic samples precisely and in a three-dimensional format, while minimizing contamination or damage that would undermine genetic analysis and PCR/STR processing.

The System of the present invention is used to separate sperm from other products (such as epithelial cells or foreign debris) in a forensic sample. However, one of ordinary skill in the art would recognize that the System may be used to separate any population of cells from another—for example, cells that have some distinction between the individual that is to have their DNA sequenced, and other individuals.

Figure 1:
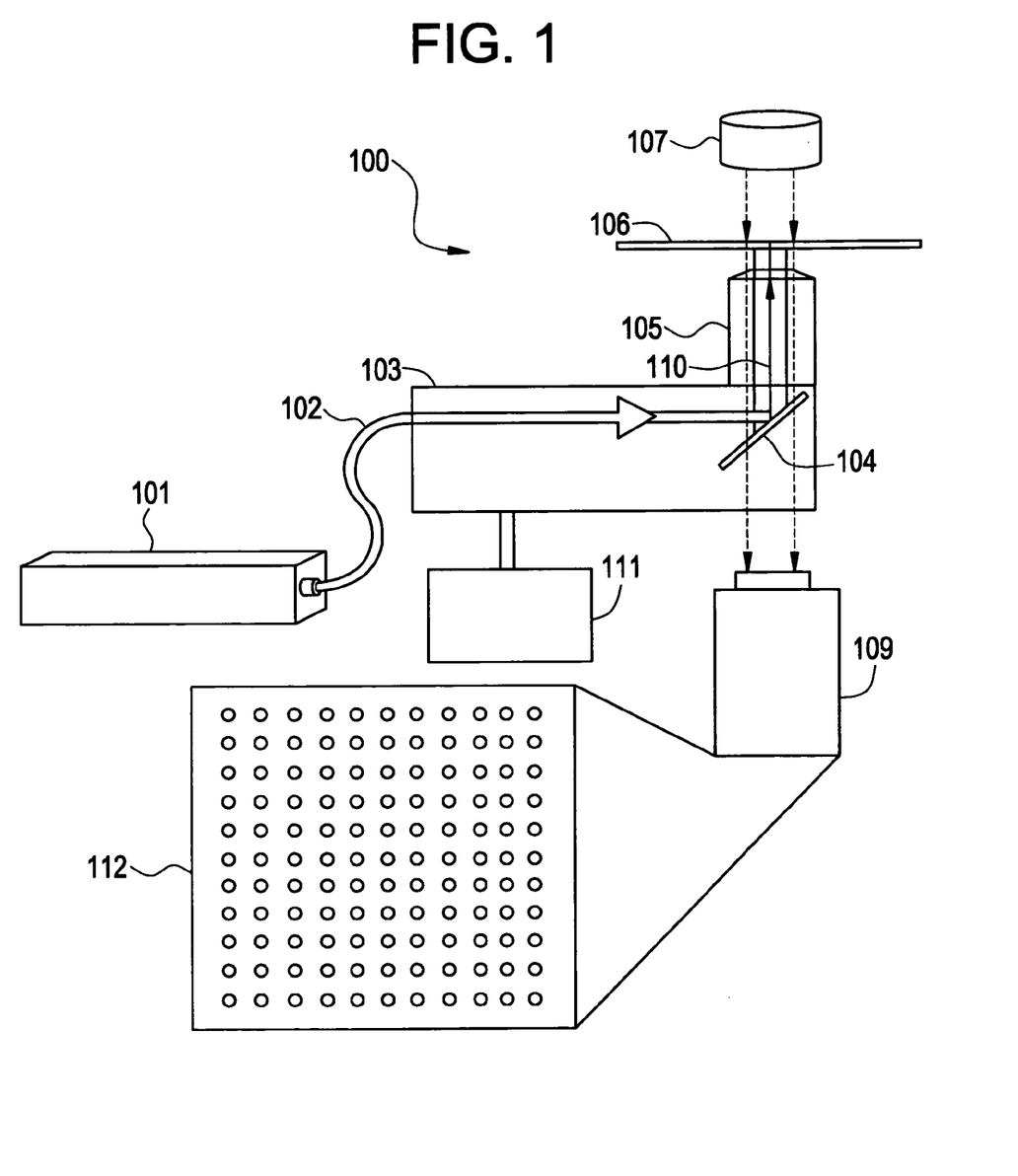
FIG. 1 depicts a diagram of an exemplary HOT system according to one embodiment consistent with the present invention.

In one embodiment consistent with the present invention, a HOT optical tweezer structure of an automated sperm cell isolator 100 is shown in FIG. 1. The HOT optical tweezer structure, for example, is described in U.S. Pat. Nos. 6,055,106, and 6,624,940, both by Grier et al., which are herein incorporated by reference.

A laser 101 provides a laser light 110 via an optical fiber 102 through a holographic optical trapping unit 103, via a dichroic mirror 104 and an objective lens 105 to a slide 106. A microscope 107 provides illumination to the slide 106. A CCD camera 109 records the images on the slide 106, which, for example, is an array of optical traps 112. The HOT system 100 is computer controlled by computer 111.

Figure 2:
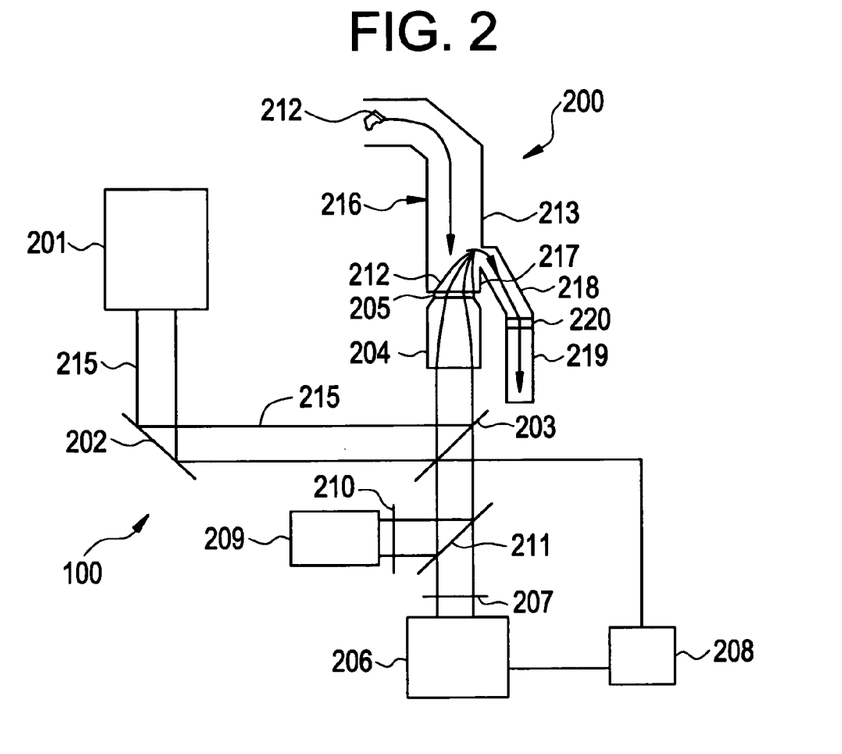
FIG. 2 depicts a diagram of an automated holographic laser extraction and purification system, which is an automated cell sorter in combination with the HOT of FIG. 1, according to one embodiment consistent with the present invention.

FIG. 2 shows one embodiment of an automated sperm cell sorter 200, consistent with the present invention, which is used to isolate the sperm cells using the HOT 100 of FIG. 1.

Specifically, a beam expanded laser 201 emits a beam 215 to a spatial light modulator 202 (or mirror with motor control in a non-HOT alternative) onto a dichroic mirror 203 (or polarizing beamsplitter—to allow imaging) which reflects the laser beam 215 through an objective lens 204 to a window 205 where the sample can be viewed. The imaging camera 206 is trained on the window 205. A filter 207 blocks laser light from reaching the camera 206 and overwhelming the camera 206 and undermining proper imaging of the sample being viewed. The camera 206 is connected to a computer control 208 with machine vision. The computer control 208 also controls the spatial light modulator 202.

In one embodiment consistent with the present invention, epi-fluorescence illumination 209 provides a beam through a filter 210 onto another dichroic mirror 211 or beamsplitter. When epi-fluorescence is done, fluorescent imaging and possibly specific labeling of cells may be used in combination with the machine vision to more easily or reliably identify the components/objects in the sample.

The components of the System 200 that are above the objective 204 are on an automated movable stage on microscope 107. The objective 204, dichroic 203, computer 206, HOT tweezing system 100, camera 206, etc. at or below objective 204 are not on the movable stage.

In one example of the automated extraction and purification System of the present invention, a forensic sample 212 (such as dried and aged swabs of semen and epithelial cells that have been rehydrated) is introduced into a flow in a tube 213. The sample 212 can be entered into a funnel, for example, which has an initial level of liquid (sterile buffer). Or, for example, the sample 212 can be entered into a channel in a plastic cartridge where the solution is inserted into an inlet or injected through a membrane or other port.

The mixed solution containing sperm, sediments the solids in the sample 212, due to gravity, into the bottom of a chamber 216. The sedimented sample 212 arrives at the bottom surface 205 of the chamber 216 which also includes a window 205 through which imaging and optical tweezing is performed. The imaging camera 206 provides viewing through the window 205, with brightfield illumination from the microscope 107, epi-illumination 209 (fluorescent or non-fluorescent), or other illumination.

Imaging identifies the sperm in the sample 212, and optical traps generated by the HOT 100 move the sperm out of the chamber 216 (which incorporates a window for observation by the HOT 100) and over a barrier 217, for example, and into an output tube 218. Once in the output tube 218, the extracted sperm is sedimented into the vial 219. In one embodiment, the vial 219 can be removed via a sterile snap-off connection from a clamping mechanism 220.

Accordingly, the sample 212 is purified to result in the desired sperm, and the unselected material which is deposited in the bottom of the chamber 216, can be collected via a purging flow, for example, for possible future analysis.

Figure 3:
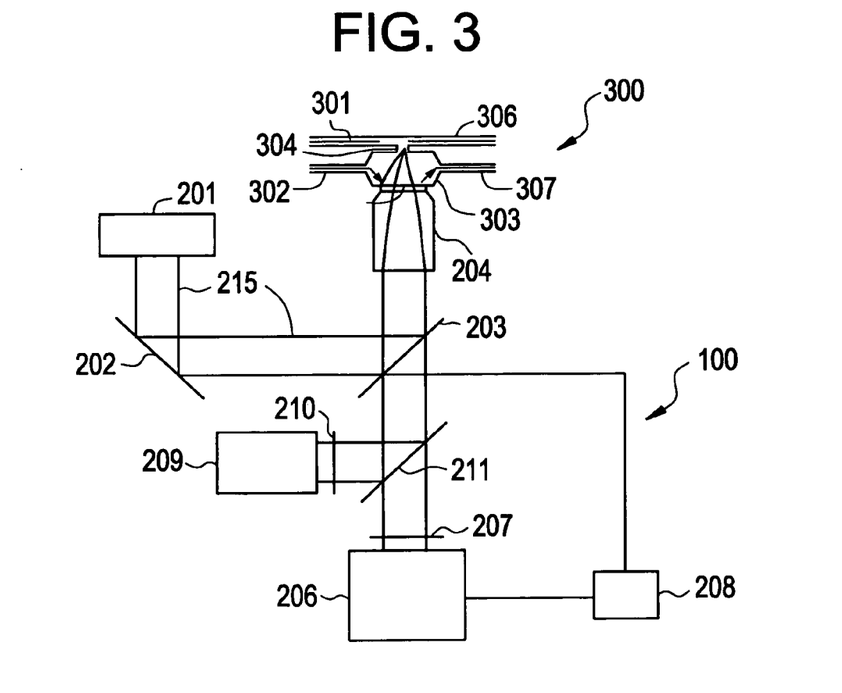
FIG. 3 depicts a diagram of an automated holographic laser extraction and purification system, according to another embodiment consistent with the present invention.

In an another embodiment of the automated extraction and purification System 300 of the present invention, as shown in FIG. 3, the HOT system 100 is similar to that shown in FIGS. 1 and 2, and the same reference numerals refer to the same elements described in FIG. 2.

However, in this embodiment, the automated sorting is performed using a slightly different structure and method. For example, in this embodiment, there are two inputs into a chamber 301—a buffer input channel 301 and a sample input channel 302. A buffer is provided into the buffer input channel 301 and flows through a relatively narrow tube or neck 304 into a reservoir/extraction region or chamber 303 and also into a collection channel 306. The buffer contacts the sample introduced through the sample input channel 302.

One or more optical tweezers may manipulate objects of interest (i.e., sperm) within the mixture in the chamber 303 (imaged via a window 305 for observation using the HOT 100), and move the desired objects to a "drop-off region" in the collection channel 306. The objects are collected and moved out through the collection channel 306 along with any buffer that did not enter into the chamber 303. The solution containing the other materials not selected, is removed via the output channel 307 from the chamber 303 for future preservation.

A flow from the buffer channels 301, 306 through the neck 304 suppresses unintended movement of material from chamber 303 into collection channel 306.

The flow into the chamber 303 may be set to be continuous or can be set to be intermittent—i.e., started/stopped. The lower surface of the chamber 303 can be treated with an anti-stick coating to avoid the sample sticking to the lower surface of the chamber 303.

Figure 4:
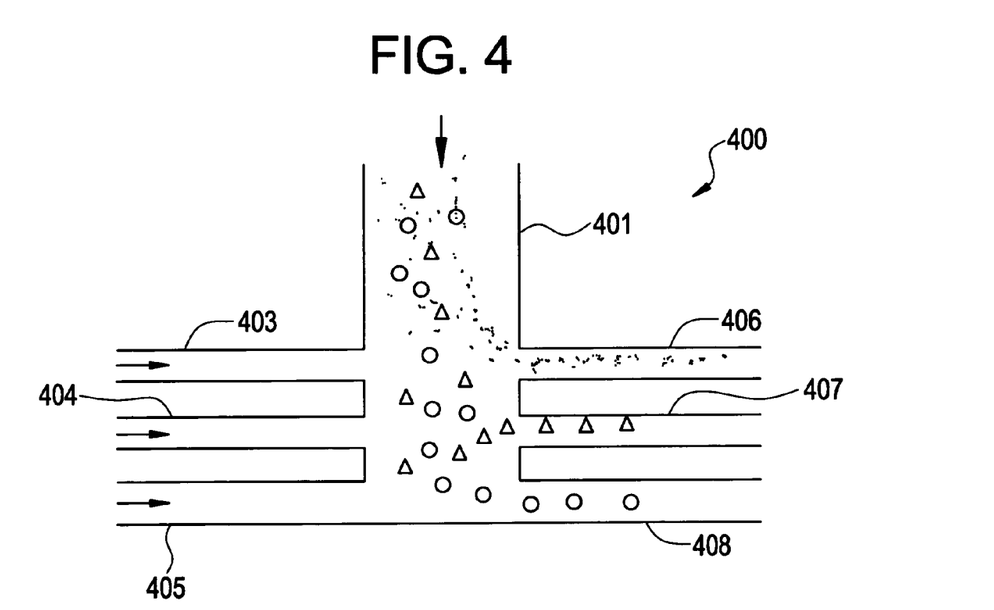
FIG. 4 depicts a diagram of another embodiment of the sorting portion of an automated laser extraction and purification system.

In yet another embodiment consistent with the present invention, FIG. 4 shows another sorting portion of an automatic extraction and purification System 400. The System 400 is similar to that of the System 300, except that the input solution enters tube 401 and sediments to the bottom of the chamber 402 by means of gravity. The three input channels 403, 404, 405 are all used for buffer solution, and mix with the sample in the chamber 402. A slow cross flow from the input channels 403-405 washes away small particles through washing output 406, and large particles fall to the bottom of the chamber 402. Selected objects are lifted into the exit flow by optical trapping, via collection output 407. Unselected objects remain near the bottom and leave via output 408.

Figure 5:
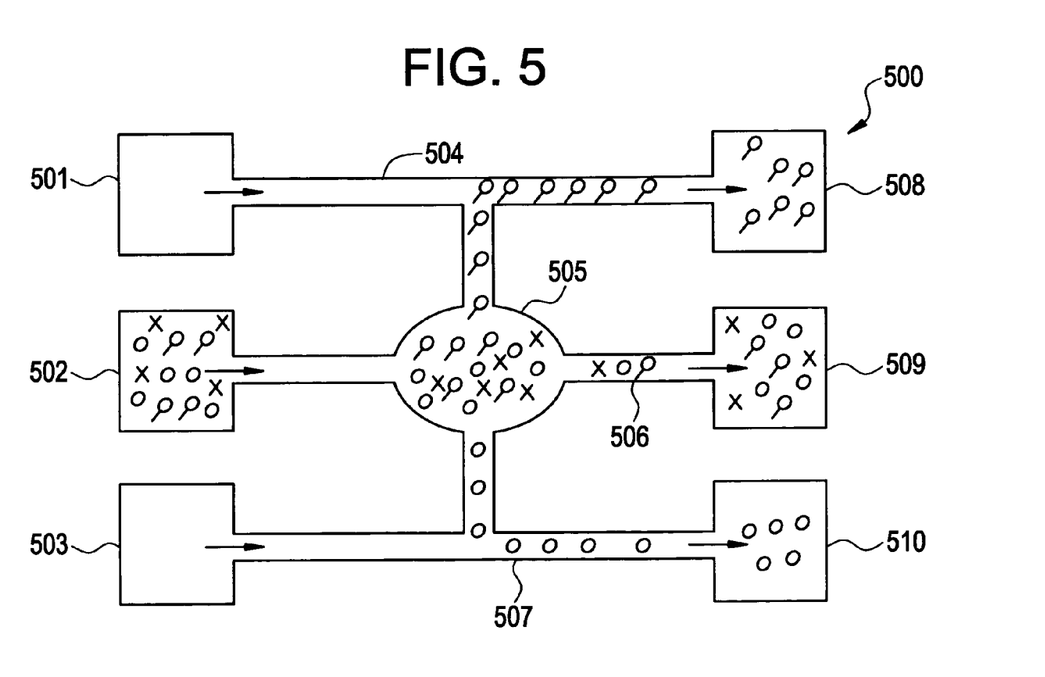
FIG. 5 depicts a diagram of yet another embodiment of the sorting portion of an automated laser extraction and purification system.

In yet another embodiment consistent with the present invention, FIG. 5 shows another sorting portion of an automatic extraction and purification System 500. The System 500 is similar to that of the Systems 300, 400, except that buffer is inputted from chambers 501, 503, and the sample is entered through chamber 502. The buffer from chamber 501 flows through channel 504 into chamber 508, and also from chamber 503 to chamber 510. The sample inputted from chamber 502 flows into larger, open intersection zone or chamber 505. There is a weak counter flow from the buffer in channels 504 and 507, into the chamber 505.

While in the chamber 505 the sample is imaged, and optical tweezers separates the sample into desired items and undesired items. For example, in a forensic sample from a rape kit, the sperm can be separated and removed via channel 504 to chamber 508, and epithelial cells can be removed via channel 507 to chamber 510. Unselected and unsorted output can be removed via channel 506 to chamber 509. The output in chambers 508-510 can be stored for further analysis.

The chamber 505 can be flushed and reloaded with a new sample.

Figure 6A:
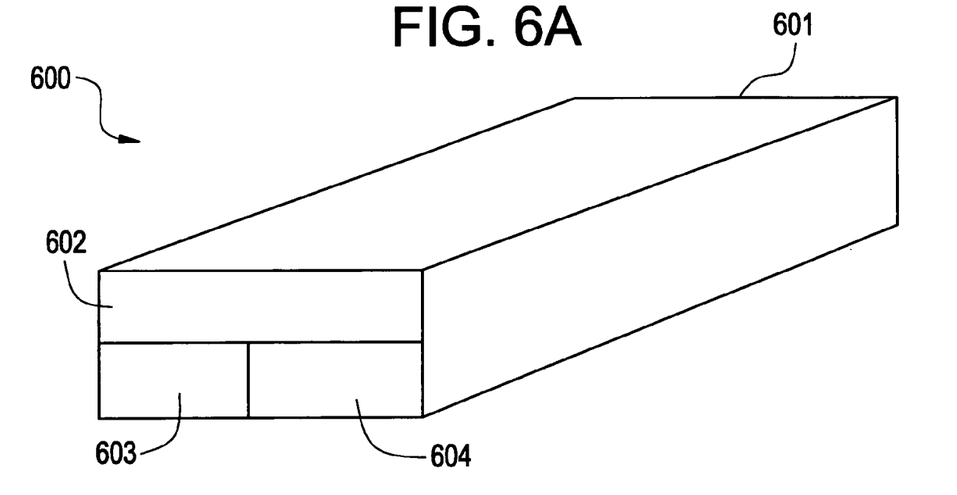
FIG. 6A depicts a perspective partial end view of yet another embodiment of the sorting portion of an automated laser extraction and purification system.

In yet another embodiment consistent with the present invention, FIG. 6A shows another sorting portion of an automatic extraction and purification System 600 using HOT 100. The sorting portion of the System 600 includes a plurality of regions or flow channels in an enclosure 601, such as buffer input channels 602, 603, and a sample solution input channel 604. A barrier 605 extends down the center of the enclosure 601 to separate the flows in 603, 604.

Figure 6B:
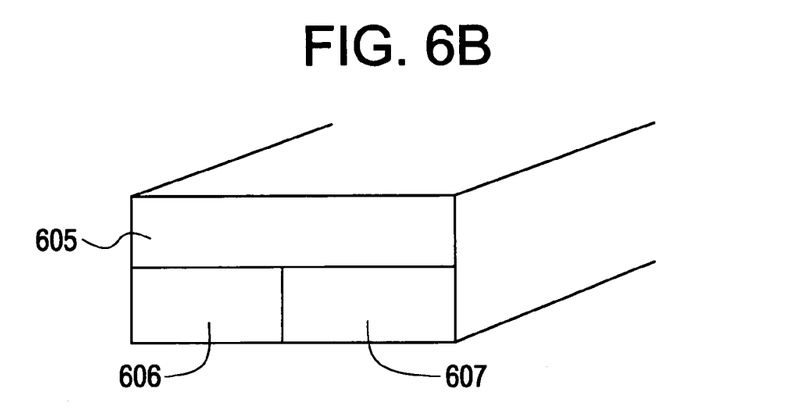
FIG. 6B depicts an end view of the embodiment of FIG. 6A.
Figure 6C:
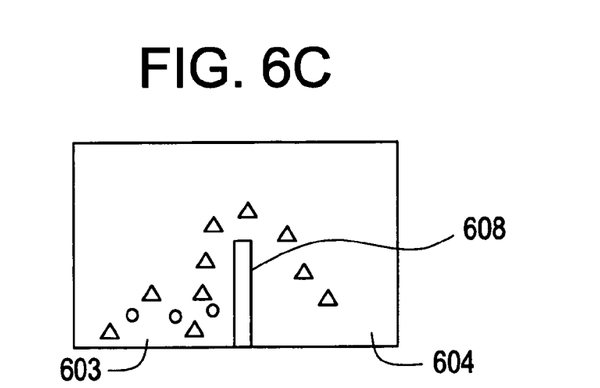
FIG. 6C depicts a cross-sectional view of the embodiment of FIG. 6A.

The flows in 603, 604 are isolated from each other by means of spaced apart regions or channels or may have a barrier 608 (see FIG. 6C) which separates the flow. In one embodiment consistent with the present invention, the flows are also isolated from the walls of the enclosure 601. This prevents sticking and accidental mixing between the flows. Materials can be optically tweezed from the solution input channel 604 into the buffer channel 603.

Collected materials are retrieved from collection output 607 (see FIG. 6B), and unselected materials are outputted at output 606. Buffer is collected at output 605.

In all embodiments, brightfield and/or fluorescent microscopy can be used to identify sperm cells. The sperm can then be moved into separate regions by optical tweezing, for extraction as a pure sample.

In addition to separating sperm in forensic sexual assault cases, the present invention allows optical tweezers to separate not just sperm, but a pure sample of cells from the victim.

Further, the present invention allows for a visual record of the processing of the sample.

Still further, the present invention allows for producing a statistical record representing the contents of each isolated sample and/or of the initial sample. For example, the number of sperm collected in sample output 1, and the number of epithelial cells collected in sample output 2, can be analyzed, and an estimate on the number/concentration of each cell or object type in the input solution can be prepared.

In operation, in all the above embodiments, the steps involved in sorting the desired material from the sample, have similarities.

In step 100, a sample 212 is obtained from the client. If the client is a rape victim, for example, a rape kit is used to obtain the sample 212, and the sample 212 will include both sperm cells, epithelial cells, and contaminants.

In step 101, the sample 212 is placed into a container/package (i.e., a rape kit) which is sterile. The sample 212 is secured once in the container.

In step 102, the container is placed into a special mount or System 200, 300. The System 200, 300, as described above and shown in FIGS. 2 and 3, as well as in the embodiments of FIGS. 4-6) include at least a sample input channel 213, 302, with a fluid means or buffer flow 213, 301 in which the sample 212 is deposited; a chamber 216, 303 where the sample 212 is separated by HOT 100; an output channel 218, 306 for the desired extracted material; and a means for removing unselected material (i.e., from chamber 216 or output channel 307).

In step 103, the sample 212 in the sealed container is introduced into the System 200, 300, by removing the sample 212 from the container and introducing it into a fluid means or buffer flow in tube 213 or channel 302, etc.

The System 200, 300 may be primed first with fluid from a fluidic buffer container 301 in one embodiment.

Further, the sample may be rehydrated prior to being introduced into the System 200, 300 by having a buffer flow through the container with the sample 212 before entering the sample 212 into an input channel.

In step 104, the flow of the sample 212 is initiated through the extraction/separation System 200, 300, into a chamber 216, 303. The flow may be gravity driven, or may be pump driven, but various means may be used for priming and driving the flow.

In step 105, the chamber 216, 303 or detection area is filled with fluid with the sample 212 therein.

In step 106, the chamber 216, 303 or detection area, which incorporates a window for observation, is imaged via microscope 107 attached to a CCD camera 109, 206—a basic machine vision system.

In step 107, the detection area (i.e., chamber 216, 303) is scanned for desired objects (i.e., sperm).

In step 108, the desired objects (i.e., sperm, sperm heads, or other relevant particles) are identified using image processing.

In step 109, optical trapping or holographic optical trapping is then used to move the desired objects (i.e., sperm vs. all other DNA containing matter) to a collection area 219, 306, which in one embodiment, has been created by introducing a clean buffer flow (i.e., collection channel 306).

Specifically, with respect to extracting sperm from the sample 212 using HOT 100, two sperm, for example, are identified among a plurality of epithelial cells, and the sperm are moved to the right of the epithelial cells using the optical tweezers. More sperm are then imaged and isolated from the epithelial cells and the surrounding solution until all the sperm have been isolated and concentrated together in a collection area.

In another embodiment consistent with the present invention, termed "lifting sperm", a plurality of sperm are simultaneously lifted above the lower surface of a microscope 107 cover glass, using optical tweezers, illustrating that multiple sperm can be manipulated in three dimensions by HOT 100. The sperm tails are only partially in focus when imaged, as they tend to fall downward and out of view. The exact positions of the optical tweezers can be shown in the software interface (i.e., as red targets).

In step 110, the sperm that has been collected using the optical tweezers, is moved into a collection channel 218, 306, via a fluidic buffer stream, and into a separated and sealed container (i.e., 219). The container can then be separated from the System 200, 300 in a manner guaranteed not to introduce contaminants (i.e., removed using a sterile snap-off connection of a clamping mechanism 220).

In an alternative step 111, the sperm collection area 216, 306 may be scanned with optical tweezers, to remove contaminants. Contaminants may be removed using the optical tweezers via the output channel 307 or purged in a purging flow from the System 200.

In yet another alternative step 112, the microscope stage 106 is automatically scanned and the detection area 216 can be swept clean with a purging flow.

In yet another alternative step 113, the chamber 216, 303 can be scanned for contaminants with the optical tweezers machine vision system 206. Any contaminants may be holographically tweezed and removed from the System 200, 300.

In an additional step in one embodiment consistent with the present invention, a software program compiles a report automatically, and the report (using image processing) is issued with feedback on sperm number and relevant performance patterns of the extracted sperm, for example.

In yet another embodiment consistent with the present invention, the above steps may be performed using holographic or non-holographic (single) optical traps.

In yet another embodiment consistent with the present invention one or more of the steps may be combined.

In another embodiment consistent with the present invention, non-diffraction limited traps may be used to tweeze only the particles of interest, i.e., to match trap size to particulate size to get preferential tweezing of the desired target.

In another embodiment consistent with the present invention, white light tweezers may be used to reduce power and cost requirements.

In another embodiment consistent with the present invention, the traps may be stationary with the stage moving, or moving with the stage steady. Scanning the stage or moving the stage would be part of the steps of locating and/or moving of the sperm.

In another embodiment consistent with the present invention, the traps may be moved holographically, or in another embodiment, with moving mirrors.

In another embodiment consistent with the present invention, the optical traps are blinked to lose material that is undesired (occasionally dropped, using the trap, so undesired material is left behind). This can cause objects with differing characteristics, such as smaller size, to be lost from the trap while the desired object is recaptured.

In another embodiment consistent with the present invention, motile and diffusive materials and cells are kept out of the output (collection) channels by using a counter flow or gravity, as described in the embodiment of FIG. 2, for example.

In another embodiment consistent with the present invention, motile cells are killed by ultraviolet light (i.e., pulsed UV laser beams), or by a chemical addition to the sample, so that they do not interfere, if they are present—with the separation process.

In another embodiment consistent with the present invention, to prevent sticking, a coating is used, or a laminating flow is used that provides a buffer zone with the walls. The coating would include a polymer coating applied by spraying a chemical solution on the surface or flowing it through the channels as in FIG. 6A.

In another embodiment consistent with the present invention, the flow in the system can be static (the stage can be moved, the fluid kept steady), dynamic (the stage is steady, the flow moves), or batch flow (flow in, stop, flow in, stop). For example, flows may be driven through all input channels and then stopped when the sample is in the sample area. The cells may then be sorted as needed by optical tweezing, and the flows may resume to flush the sorted materials into the output channels and refill the sample area with new solution to be sorted. This process can be iterated repeatedly as needed.

In batch processing, a portion of a sample is introduced into the System 200, 300, the portion is operated on so as to separate the desired materials (by optical tweezing), and another portion of the sample is introduced into the System 200, 300. This allows more sample volume to be introduced to the System 200, 300 than the System 200, 300 itself can hold, and can reduce the amount of sample that needs to be analyzed before acquiring a desired number of output cells.

In yet another embodiment consistent with the present invention, the separation of the sperm is performed using flow switching. In this embodiment, flow switching is accomplished where three inputs channels that move buffer solution, input solution, and buffer solution, respectively, into a tube where inspection of the sample is performed with lasers, optically, or any other method.

For example, optical trapping in a microscopic area of the tube separates the sperm from a forensic sample, and the sperm is moved to a collection output channel. By switching the control flow quickly from the collection output channel to another output channel, the unselected cells etc. can be removed from the other output channel.

Switching may be done using mechanical actuators, membranes, capacitive methods, thermal heating, thermal creation or expansion of a bubble or other techniques. In the output collection channel and output channel (which are large scale compared to the microscopic inspection region), small time-dependent flow rate changes cause steering of the objects between outputs.

In another embodiment consistent with the present invention, the particles can be steered using flows instead of optical trapping.

In yet other embodiments consistent with the present invention, the sperm can be identified using various microscopy techniques for imaging objects and properties of objects, including: imaging processing using bright field imaging, DIC (differential interference contrast), phase contrast, spectral imaging epi-illumination brightfield, fluorescence imaging, and polarized light; spectroscopy; light scattering—for example, looking for asymmetric light scattering profiles; and non-imaging optical probing (where an object's response to an optical trap is noted—for example, a sperm aligning on its end in response to a light pattern).

The present invention may be used to separate any type of cells. For example, different cell types might be one form of distinction. Another form of distinction might be a difference in gender of the cell types. For example, Hoescht staining of DNA may be used to label DNA and differences in quantity of DNA may be measured to identify male or female cells. In addition, other markers, such as fluorescent markers, may be used to distinguish the cells.

For example, suppose the cells represent three people. This could be sperm from two assailants. Or it could be a piece of fabric with the victim, assailant, and a random third person who came in contact with the fabric—perhaps even of technician or police officer even. Some could even be animal cells. Using any sort of fluorescent labeling or other technique to help distinguish cell types and fractionate the cells into multiple pure fractions would be advantageous.

In addition, to the sorting and manipulation capabilities of HOT, HOT lasers can themselves be used as particle probes. The lasers can be used to identify cellular properties, or physical properties of particles. Differences amongst objects, including light transmittance, light absorbance, light reflectance, mass, size, shape, index of refraction, membrane properties, and malleability create differences in the objects' movement and shapes when interacting with optical traps and light patterns. The behavior of objects in traps can hence be used to distinguish objects with differing properties.

Also, the System 200, 300 of the present invention, can be used in either a user-interactive mode with the user doing the image processing/selection steps and maybe even the flow control, or it can be programmed, using machine vision, for a virtually unlimited set of manipulation tasks. In the latter, the computer can visually identify cells of interest and calculate HOT trap movement sequences to remove the desired objects from the sample. Image processing-based trap movement obviates the need for user interaction if the parameters of the system are carefully tailored to manipulate particular objects of interest.

As described above, the present invention impacts a wide variety of forensic applications by its use of HOT technology. In particular, the present invention allows automatic collection of sperm cells for STR PCR testing in sexual assault cases. Because of the large number of holographic traps that the system generates, the light can act as a perfect filter, separating objects based on size, shape, or other properties. Although machine vision is used to choose what cells to separate, passive filtering is also an option.

Optical tweezing of forensic samples means that sperm cells can be isolated from a victim's epithelial cells, and then introduced into a separate chamber for DNA analysis. The process is completely automated, involving sealed chambers so that cross-contamination is minimized or nonexistent. Further, the purity of the extracted sample and reliability of the process is a major advantage. Further, the record-keeping by imaging or video is also of great benefit, as well as the ability to store the extracted or purified samples for future analysis.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A method of purifying a sample in an automated extraction and purification system which uses optical tweezers, comprising:
    introducing the sample in a sample solution, into a first input channel;
    introducing a buffer solution into a second input channel adjacent to said first input channel;
    providing a barrier along the length of and between said first input channel and said second input channel such that said sample solution and said buffer solution are completely separated;
    using the optical tweezers to generate optical traps which move selected particles of the sample from said first input channel over said barrier at any position along said first input channel, into said second input channel;
    collecting said selected particles at an output of said second input channel; and
    collecting unselected particles at an output of said first input channel.

2. The method according to claim 1, further comprising:
    identifying the selected particles by image processing using a machine vision system.

3. The method according to claim 2, wherein imaging of the particles using the machine vision system, is automated and a visual record can be maintained.

4. The method according to claim 1, wherein the optical tweezers is a holographic optical trapping system.

5. The method according to claim 1, wherein the optical tweezers utilize a non-holographic optical trapping system.

6. The method according to claim 1, wherein a report is automatically generated to provide information on the selected particles.

7. The method according to claim 5, wherein non-diffraction limited optical traps generated by the optical trapping system, may be used to tweeze only the selected particles.

8. The method according to claim 1, wherein the optical tweezers are white light optical tweezers.

9. The method according to claim 4, wherein said holographic optical trapping system is used with a stage for mounting of its components, and the stage is movable.

10. The method according to claim 4, wherein holographic optical traps generated by the holographic optical trapping system, are blinked to lose the unselected particles.

11. The method according to claim 4, wherein the unselected particles are killed by one of ultraviolet light and a chemical addition to the sample.

12. The method according to claim 1, further comprising:
    coating walls of said first input channel and said second input channel to prevent sticking of the particles to said walls.

13. The method of claim 4, further comprising:
    probing the sample to determine the composition of the particles using lasers of the holographic optical trapping system.

14. The method according to claim 1, wherein the selected particles are at least one of sperm or epithelial cells.

15. The method according to claim 4, wherein the system is user controlled.

16. The method according to claim 1, wherein said first input channel and said second input channel are disposed within an enclosure.

17. The method according to claim 1, wherein a third input channel is disposed above said first input channel and said second input channel, and buffer solution is introduced therein.

18. The method according to claim 17, wherein buffer solution is collected at an output of said third input channel.

19. The method according to claim 1, wherein the sample is a forensic sample.

* * * * *